United States Patent [19]
Mitchell et al.

[11] Patent Number: 5,749,840
[45] Date of Patent: *May 12, 1998

[54] DYNAMIC SPLINT

[75] Inventors: Andrew L. Mitchell, Wilmington, Del.; Kenneth A. Patchel, Chadds Ford, Pa.

[73] Assignee: Ultraflex Systems, Inc., Malvern, Pa.

[*] Notice: The term of this patent shall not extend beyond the expiration date of Pat. No. 5,358,469.

[21] Appl. No.: 550,603

[22] Filed: Oct. 31, 1995

Related U.S. Application Data

[62] Division of Ser. No. 443,200, May 17, 1995, Pat. No. 5,658,241, which is a continuation of Ser. No. 210,763, Mar. 22, 1994, abandoned, which is a continuation-in-part of Ser. No. 740,387, Aug. 5, 1991, Pat. No. 5,358,469, which is a continuation-in-part of Ser. No. 447,460, Dec. 7, 1989, abandoned.

[51] Int. Cl.$^6$ .................................................. A61F 5/00
[52] U.S. Cl. ............................ 602/5; 602/23; 602/26
[58] Field of Search ................................ 128/846, 882; 602/5, 13, 23, 26, 27, 61, 62

[56] References Cited

U.S. PATENT DOCUMENTS

| | | |
|---|---|---|
| 288,239 | 11/1883 | Ingram . |
| 2,067,567 | 1/1937 | Gruca . |
| 2,832,334 | 4/1958 | Whitelaw . |
| 3,607,963 | 9/1971 | Dannell et al. . |
| 3,826,251 | 7/1974 | Ross . |
| 4,340,041 | 7/1982 | Frank . |
| 4,370,977 | 2/1983 | Mauldin et al. . |
| 4,397,308 | 8/1983 | Hepburn . |
| 4,485,808 | 12/1984 | Hepburn . |
| 4,489,718 | 12/1984 | Martin . |
| 4,508,111 | 4/1985 | Hepburn . |
| 4,538,600 | 9/1985 | Hepburn . |
| 4,614,181 | 9/1986 | Karlsson . |
| 4,624,247 | 11/1986 | Ford . |
| 4,657,000 | 4/1987 | Hepburn . |
| 4,697,583 | 10/1987 | Mason et al. . |
| 4,726,361 | 2/1988 | Farley . |
| 4,771,768 | 9/1988 | Crispin . |
| 4,817,588 | 4/1989 | Bledsoe . |
| 4,844,057 | 7/1989 | Hoy . |
| 4,846,842 | 7/1989 | Connolly et al. . |
| 4,865,024 | 9/1989 | Hensley et al. . |
| 4,982,732 | 1/1991 | Morris . |
| 5,000,169 | 3/1991 | Swicegood et al. . |
| 5,002,044 | 3/1991 | Carter . |
| 5,013,037 | 5/1991 | Stermer . |
| 5,025,801 | 6/1991 | Callaway . |
| 5,052,379 | 10/1991 | Airy et al. . |
| 5,092,321 | 3/1992 | Spademan . |
| 5,103,807 | 4/1992 | Makaran . |
| 5,358,469 | 10/1994 | Patchel et al. . |

*Primary Examiner*—Michael A. Brown
*Attorney, Agent, or Firm*—Sixbey, Friedman, Leedom & Ferguson; Daniel W. Sixbey

[57] ABSTRACT

A dynamic splint is provided which applies a bias force across a body joint with a magnitude which is adjustable at a pivot in the splint. At the pivot, a joint enclosure is provided to house a coiled leaf spring having one end connected to a movable adjustment mechanism. The relative magnitude of the bias is indicated by an indicator bearing numeric markings which moves with movement of the adjustment mechanism. A pin lock mechanism is provided for locking pivoted strut members of the splint to prevent relative movement thereof about the pivot.

24 Claims, 4 Drawing Sheets

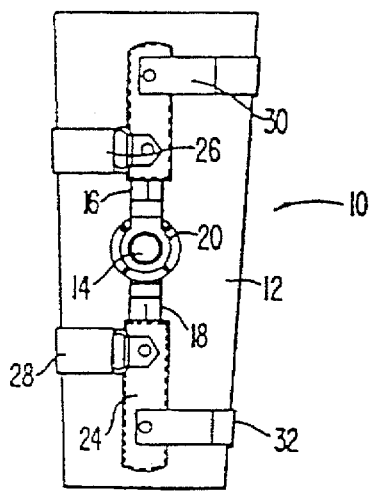
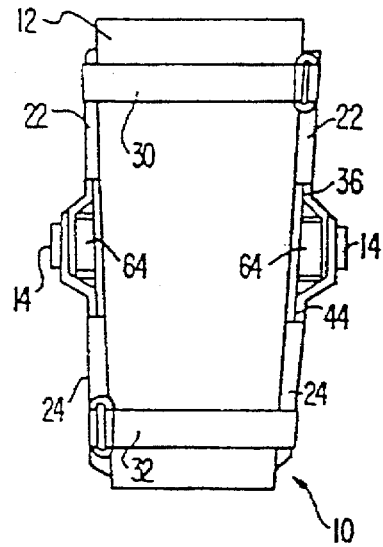
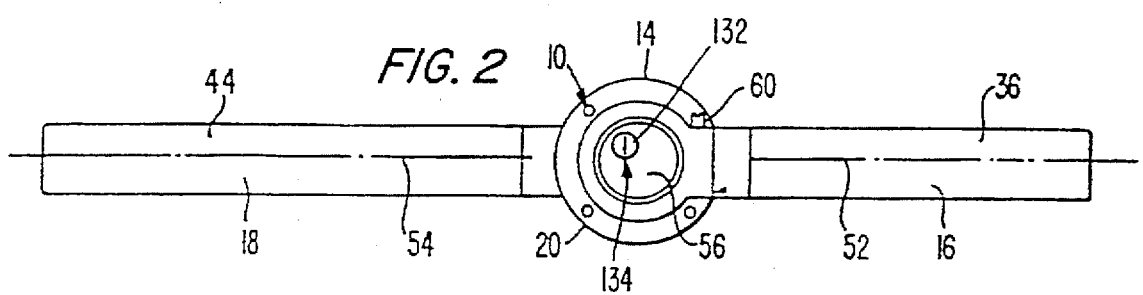
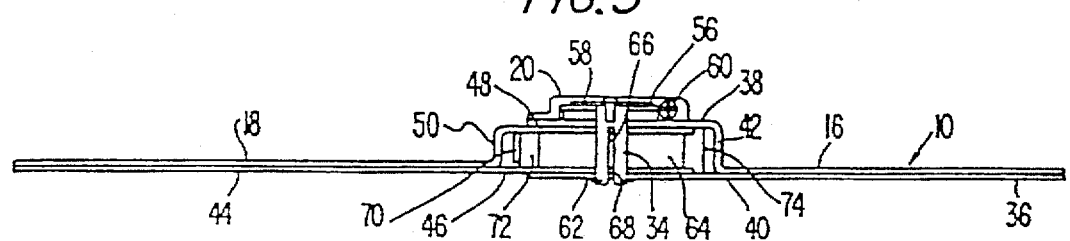

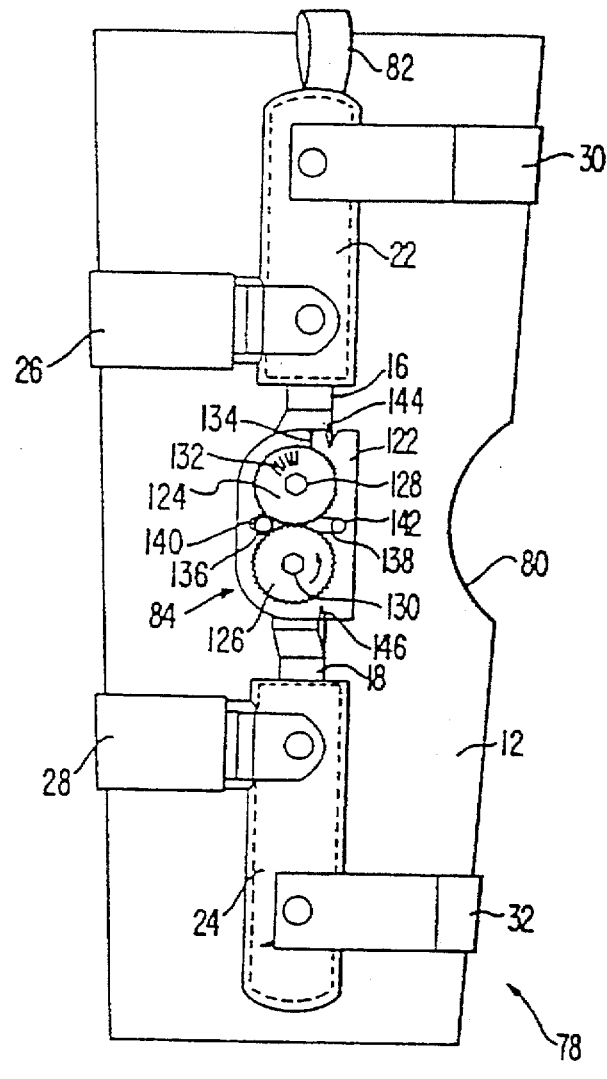
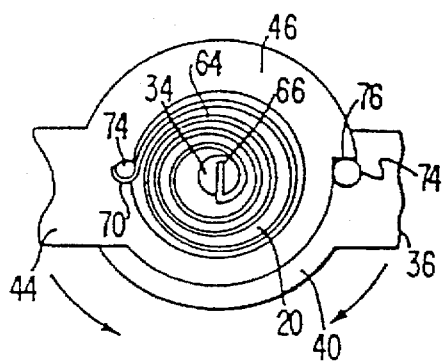
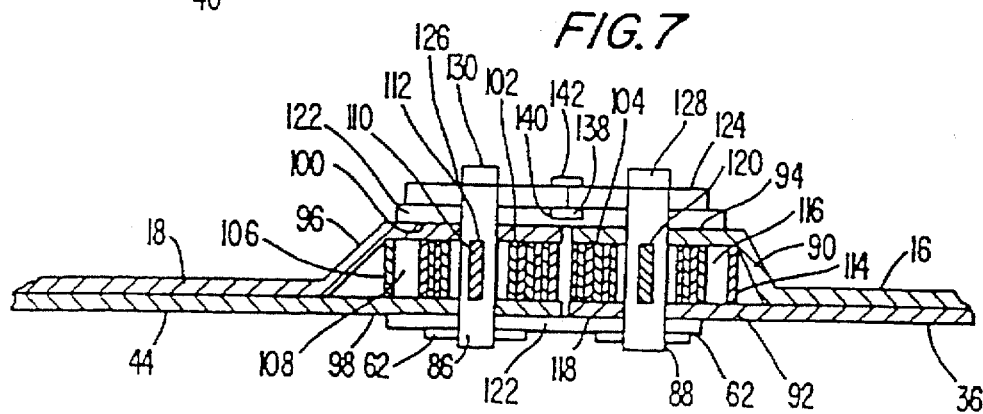

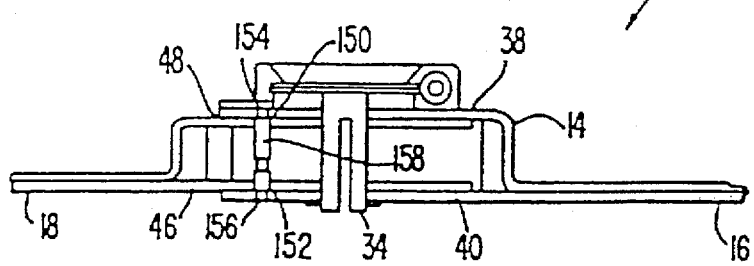
FIG. 8
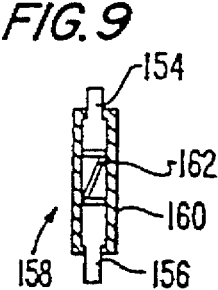
FIG. 9
FIG. 10
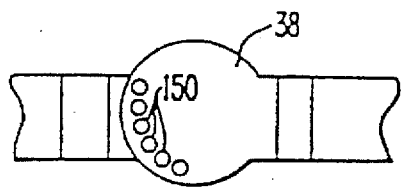
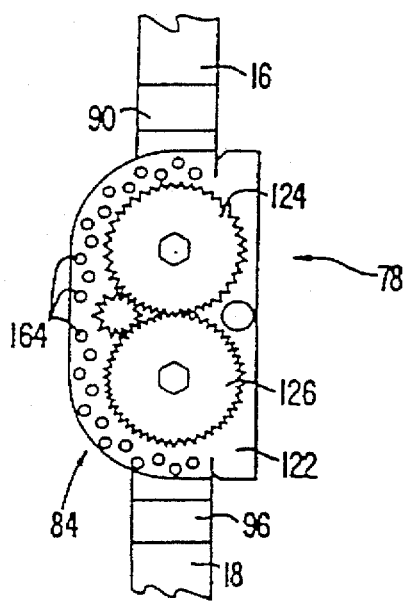
FIG. 11
FIG. 12
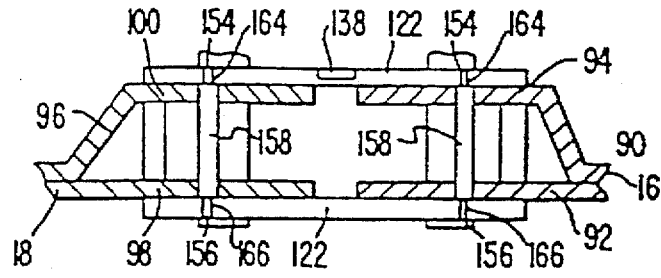

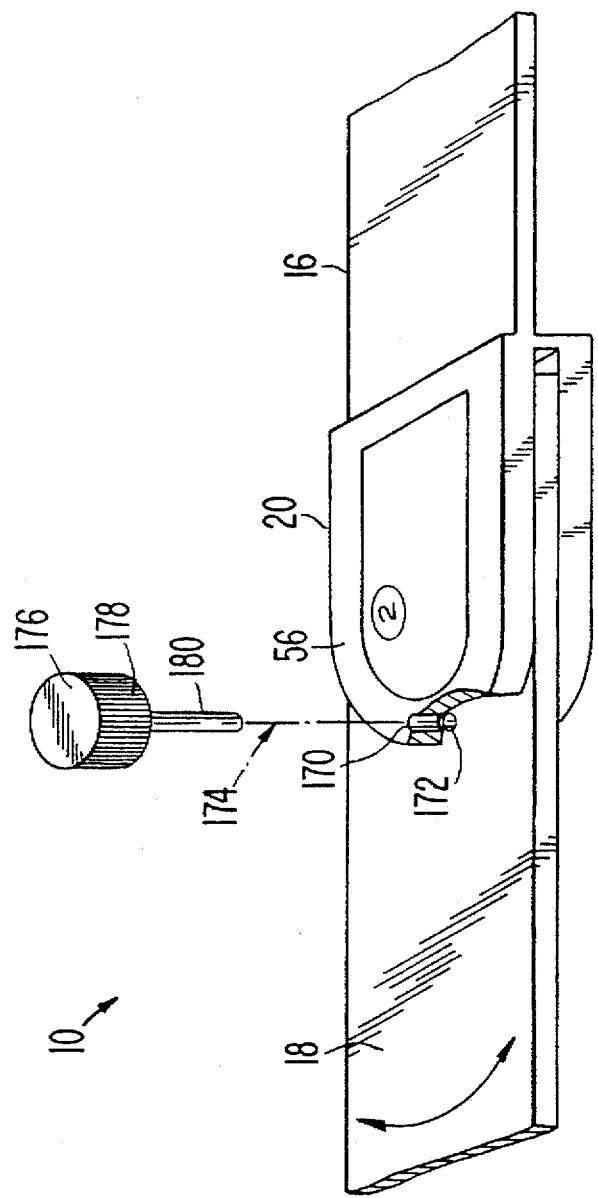

DYNAMIC SPLINT

The present application is a divisional application of U.S. Ser. No. 08/443,200 filed May 17, 1995, now Pat. No. 5,685,241, which is a continuation of U.S. Ser. No. 08/210,763 filed March 22, 1994, now abandoned, which was a continuation-in-part of U.S. Ser. No. 07/740,387 filed Aug. 5, 1991, now U.S. Pat. No. 5,358,469, which was a continuation-in-part of U.S. Ser. No. 07/447,460 filed Dec. 7, 1989, now abandoned.

FIELD OF THE INVENTION

The present invention relates to splint assemblies generally, and more particularly to a dynamic splint adapted to exert an adjustable force or tension at a body joint.

BACKGROUND OF THE INVENTION

In recent years, dramatic advances have been made in the development of lightweight, compact mechanisms for correcting common and debilitating injuries to body joints such as fingers, wrists, knees, elbows and the like. Perhaps the greatest advances have been made in the design of orthotic brace units which counteract instabilities in a joint by reinforcing the joint as a whole to prevent unwanted motion. Such orthotic devices are typically formed with a mechanical joint supported by a pair of bracing members. The mechanical joint is defined by a pair of side bars, each of which has a hinge-like pivoting joint in its middle with the top and bottom ends of the side bars being connected to bracing members which fit around a body portion above and below the joint to be supported. These devices operate generally by confining the movement of the joint as it bends so that unwanted motions are eliminated or at least minimized. The most commonly known orthoses are orthotic knee braces of the type commonly used by athletes who have suffered injuries to either the ligaments that interconnect the lower femur and upper tibia, or to the bones themselves, which result in knee instabilities.

Joint instability is not the only debilitating condition of a body joint which requires correction. The operation of a body joint may be impaired in a manner which inhibits the operation of the joint in accomplishing extension or flexion. For example, a flexion contracture prevents full extension of the joint, while an extension contracture prevents the joint from being bent or flexed to the full extent. Obviously, the treatment of a flexion contracture or an extension contracture requires more than the mere support against instability provided by many conventional orthotic devices.

To treat flexion and extension contractures, spring-biased splint units have been developed to provide a force across a body joint. These splint devices provide tension which operates in opposition to a flexion or extension contracture and thereby not only provide support in instances where muscular weakness exists, but also enhance rehabilitation. One type of known adjustable spring-loaded splint includes a pair of lower struts and a pair of upper struts of tubular configuration which are pivotally interconnected. Spring biasing units mounted within the tubular struts are adapted to apply an adjustable force at the pivot point which tends to align the two pivoted struts. Such an adjustable splint mechanism is illustrated by U.S. Pat. Nos. 4,397,308; 4,485,808; 4,508,111; 4,538,600 and 4,657,000 to George R. Hepburn.

Although known adjustable splints operate effectively to apply tension across a joint, they are relatively heavy and bulky and consequently impede to some extent free activity at the affected joint. The heavy tubular strut assemblies used in prior art splints are generally not coextensive from the connecting pivot point, and thus may be brought into only parallel rather than axially aligned relationship. It is impossible to contour these heavy struts to conform to the limb of a user, and the degree of pivotal movement within which the applied force is linear is generally small. Such splints generally use straight line springing against a cam. The rotational force applied by the cam is extremely non-linear due to the changing moment arm on the cam surface. This variation prevents the application of a constant therapeutic force and requires constant adjustment to the spring force through the desired range of motion.

Finally, with known prior art adjustable splints, the bias adjustment mechanism for the splint is difficult to reach, and the degree of adjustment is often difficult to ascertain. Accurate adjustment of the bias for such prior art units with the splint in place is not easily accomplished, and the bias structure employed does not facilitate polycentric joint structures of the type better suited to the motion of certain joints, such as the knee.

In general, prior art splints have been constructed for force application in either a flexion or contraction direction, but not both. However, U.S. Pat. No. 4,370,977 to Mauldin shows a knee brace with a spring connected to a hinge member which may be used to resist motion in either direction. Resistance in one direction is transformed to resistance in the opposite direction by removing a thumbscrew and the torsion spring, and reinstalling the torsion spring in different holes on the hinge portion. However, mechanisms of this type do not provide an even adjustment of force capability, and reversing the direction of force application requires complexity in the operations required to reverse the device.

U.S. Pat. No. 5,052,379 to Airy et al. shows a brace with frame sections connected by a pivot joint which resists relative movement of the frame sections in either or both directions about the pivot axis. A removably connected torsion spring provides the resistive force. This reference, however, uses different torsion springs to impose the resistance desired, rather than changing the position of a single torsion spring.

SUMMARY OF THE INVENTION

It is a primary object of the present invention to provide a novel and improved dynamic extension or flexion splint for the treatment of joint contractures which is easily applied to a body member in the area of the joint to be treated and which is both compact and lightweight.

Another primary object of the present invention is to provide a mechanism for applying an accurate adjustable force with near-constant linearity opposing movement of a body joint, consistent reset-ability and easy read-ability.

Another object of the present invention is to provide a novel and improved dynamic extension or flexion splint having opposed strut assemblies which incorporate flat strut members adapted to be contoured in place to conform to a body member. This permits customizing the fit of the splint for greater comfort.

A further object of the present invention is to provide a novel and improved dynamic extension and/or flexion spli having opposed strut assemblies which may be easi removed from a strut assembly support unit. Each st assembly includes two elongated strut members which sl into pockets on either side of the joint to be treated.

Yet another object of the present invention is to pr a novel and improved dynamic extension and/or flex at which provides a full range of motion for a joint under treatment. The splint incorporates strut members which pivot at a mechanical joint through the maximum anatomical range plus 10° hyperextension. Tension is applied to the strut members by a torsion or power-spring type of biasing unit with near linear force characteristics mounted at the mechanical joint, and the spring tension is adjustable by means of a bias adjustment mechanism which is also located at the mechanical joint. Thus, the tension applying spring and the bias adjustment are both located entirely at the mechanical joint for the splint.

A further object of the present invention is to provide a novel and improved dynamic extension and/or flexion splint having a polycentric joint mechanism which is adapted to provide greater than the full anatomical range of motion. Elongated strut members are mounted on the joint for pivotal motion about two spaced parallel pivot axes. Each strut member is biased by a separate spring, and the bias of plural springs is simultaneously adjusted by a bias adjustment mechanism. An indicator at the mechanical joint provides an indication of the degree of bias which is set into the springs.

A still further object of the present invention is to provide a dynamic extension and/or flexion splint having an adjustable spring mechanism which is reversible to provide either flexion or extension resistance.

Another object of the present invention is to provide an adjustable-bias dynamic extension and/or flexion splint with a visible indicator showing the relative magnitude of the bias force applied.

A further object of the present invention is to provide an adjustable-bias dynamic extension and/or flexion splint wherein the bias force is produced by a mechanism in a housing located at the joint, and a visible indicator of the relative magnitude of the bias force is provided when different inscribed portions of a member rotating upon bias force adjustment become visible through an aperture as a result of the rotation.

It is also an object of the present invention to provide a dynamic extension and/or flexion splint, having portions attachable to a human body on each side of a body joint and applying a bias force to the joint, which also has a mechanism for selectively negating the bias force during attachment or removal of the splint.

A still further object of the present invention to provide a dynamic extension and/or flexion splint, having portions attachable to a human body on each side of a body joint and applying a bias force of adjustable magnitude to the joint, which also has a mechanism for selectively negating the bias force during attachment or removal of the splint without changing the magnitude adjustment setting the bias force to be applied.

These, and other objects of the present invention are accomplished by providing an adjustable splint having a pair of elongated strut assemblies which each incorporate a pivotal joint between the ends thereof. These strut assemblies are supported on opposite sides of a body joint by a strut support unit which is mountable on a body member and which locates the pivotal joint in alignment with a body joint. Each strut assembly includes a first elongated strut member and a second elongated strut member which extend from the pivotal joint. The elongated strut members of each strut assembly are flat units which may be contoured to match the contour of the body member upon which the splint is mounted. The pivotal joint operates to connect one end of the first and second strut members for pivotal movement about a pivot axis between a first extended position where the elongated strut members extend outwardly from opposite sides of the pivotal joint and a second closed position where the first and second strut members extend outwardly in close proximity from the same side of the pivotal joint. A bias unit is provided at the pivotal joint to oppose pivotal movement of the strut members in a first direction and to aid such pivotal movement in a second opposite direction. The magnitude of the bias is adjustable by a mechanism which is also located at the pivotal joint, while the range of motion provided by the joint can be altered by spring loaded pins which operate as stops for the strut members. The relative magnitude of bias provided is indicated in a preferred embodiment by numeric markings on a rotating member of the adjustment mechanism. The portion of the rotating member having the appropriate magnitude marking is visible through an aperture in the housing. A pin lock mechanism is provided for locking the strut members to prevent relative movement thereof and to temporarily prevent the application of force by the bias unit during attachment and removal of the splint.

The dynamic splints disclosed permit maintenance of a defined tolerable force level with near constant linearity over a wide range of motion of a body joint. The dynamic splints are particularly useful for prophylactic maintenance of range-of-motion and mobility, particular in post-operative cases.

BRIEF DESCRIPTION OF THE DRAWINGS

FIG. 1 is a view in side elevation of the dynamic extension splint of the present invention;

FIG. 2 is a plan view of a strut assembly for the dynamic extension splint of FIG. 1;

FIG. 3 is a sectional view of the strut assembly of FIG. 2;

FIG. 4 is a view in front elevation of the strut assembly of FIG. 1;

FIG. 5 is a sectional view of a biasing spring assembly used in the strut assembly of FIG. 3;

FIG. 6 is a view in side elevation of a second embodiment of the dynamic extension splint of the present invention;

FIG. 7 is a sectional view of a strut assembly for the dynamic extension splint of FIG. 6;

FIG. 8 is a sectional view of the strut assembly of FIG. 2 showing a range of motion stop assembly;

FIG. 9 is a sectional view of a spring loaded pin used in the range of motion stop assembly of FIG. 8;

FIG. 10 is a partial plan view of the strut assembly of FIG. 8;

FIG. 11 is a partial plan view of a strut assembly for the dynamic extension splint of FIG. 6 showing a range of motion stop assembly;

FIG. 12 is a partial sectional view of the strut assembly of FIG. 11; and

FIG. 13 is a side view of a locking pin according to the present invention, installed through the housing and into the strut assembly to prevent relative rotation of the struts.

DESCRIPTION OF THE PREFERRED EMBODIMENTS

Referring now to FIGS. 1–5, the dynamic extension and/or flexion splint of the present invention indicated generally at 10 includes a suspension sleeve 12 formed from neoprene foam or similar material having some elasticity. The suspension sleeve is adapted to fit snugly around a limb or other body member in the area of a joint and operates to position a mechanical joint assembly 14 in alignment with a body joint. Suspension sleeve 12 provides a slight compression to the body member in the area of the affected body joint. This compression, and heat associated therewith, facilitates tissue nutrition which facilitates tissue growth.

A pair of mechanical joint assemblies 14 are mounted upon opposite sides of the suspension sleeve 12 as illustrated in FIG. 4, and each mechanical joint assembly includes first and second strut members 16 and 18 which extend outwardly from a mechanical joint 20 which is a hinge structure. The strut members 16 and 18 are removably received in open ended, spaced pockets 22 and 24, respectively, and a pair of such pockets are secured to each of two opposite sides of the suspension sleeve 12. These pockets may be formed of leather or similar material, and operate to facilitate removal of a mechanical joint assembly 14 therefrom. When the mechanical joint assembly is in place within the pockets 22 and 24, the mechanical joint 20 will be retained in position at the side of a body joint to be treated. Adjustable posterior straps 26 and 28 and anterior straps 30 and 32 are secured to the pockets 22 and 24. The combination of an anterior and posterior strap is positioned on either side of the mechanical joint 20, and these straps cooperate to surround the limb of a user on either side of a joint to be treated. Such anterior and posterior straps insure that optimum therapeutic effectiveness is obtained from the spring tension provided by the mechanical joint 20.

The mechanical joint 20 is formed at ends of the strut members 16 and 18 which are pivoted about a pivot post 34. These pivoted ends of the strut members are bifurcated to provide an enclosure for an adjustable spring mechanism used to tension the mechanical joint 20. Thus, the first strut member 16 consists of a flat, elongate strut section 36 which, as it approaches the mechanical joint 20, is split into an upper leg 38 and a lower leg 40. The upper leg extends parallel to and is spaced from the lower leg by a bridging section 42. Similarly, the second strut member 18 includes a flat, elongate strut section 44 having a bifurcated end with a lower leg 46 which extends parallel to but is spaced from an upper leg 48 by a bridging section 50. The upper and lower legs 38 and 40 and the upper and lower legs 46 and 48 are arcuate in configuration, as illustrated by the lower legs 40 and 46 shown in FIG. 5. The upper legs 38 and 48 substantially match the lower legs in configuration.

As illustrated in FIG. 3, the legs 46 and 48 fit within the legs 38 and 40, and are mounted for pivotal movement by the pivot post 34 which extends therethrough. This pivot post creates a pivotal axis which is substantially perpendicular to the longitudinal axes 52 and 54 of the strut sections 36 and 44, respectively.

A gear housing 56 is secured to the outermost surface of the upper leg 38, and operates to enclose a gear 58 mounted upon one end of the pivot post 34. This gear meshes with an adjustment screw 60 which is mounted for rotation in the gear housing 56. The adjustment screw has threads which engage the teeth of the gear 58 in known manner to rotate the gear and thereby rotate the pivot post 34. However, when the adjustment screw 60 is stationary, it locks the gear and the pivot post to the upper leg 38 and the lower leg 40. However, the lower leg 46 and upper leg 48 are mounted for pivotal movement about the pivot post 34.

As will be noted from FIG. 3, the pivot post extends completely through the upper legs 38 and 48 and the lower legs 40 and 46, and is held in place by a removable clip 62 which engages a groove in the pivot post. This removable clip may be formed by a spring clip, washer, or other known removable clip means, which can be removed from a groove in the pivot post 34 to facilitate disassembly of the mechanical joint 20. This permits a circular leaf-spring 64 to be mounted about the pivot post 34 between the lower and upper legs 46 and 48. One end 66 of this circular leaf-spring is secured within a central slot 68 formed in the pivot post 34, while an opposite end 70 of the leaf-spring is hooked about a post 72 which extends between the lower leg 46 and the upper leg 48. A second post 74 extends between the upper leg 38 and the lower leg 40, and this post is engaged by a step 76 formed in the periphery of the lower and upper legs 46 and 48 when the flat elongate strut sections 36 and 44 are in the extended position of FIG. 2.

The degree of tension set into the circular leaf-spring 64 may be indicated by indicia 132 on the gear 58 which cooperates with a stationary indicator 134 formed on the gear housing 56. Specifically, gear 58 may be marked about its periphery with a series of numbers or other markings indicating the relative tension existing on the spring when that marking occupies a defined position. Stationary indicator 134 may take the form of an aperture in gear housing 56 through which indicia 132 (i.e. the numbers or other markings) are visible.

As will be noted from FIG. 5, when the flat elongate strut sections 36 and 44 are pivoted toward one another in the direction of the arrows in FIG. 5, the steps 76 will move away from the post 74 and the pivotal movement will be opposed by the tension of the circular leaf-spring 64. Thus, the flat, elongate strut sections move from an extended position with the steps 76 in contact with the post 74 against the bias of the spring 64 to a second closed position wherein the first and second strut members come into contact and extend from the bottom side of the mechanical joint 20 in FIG. 5. As the flat elongate strut sections 36 and 44 are pivoted back to the extended position shown in FIG. 2, the pivotal movement is aided by the bias of the spring 64. It is obvious that this bias may be adjusted by rotating the adjustment screw 60 which in turn engages and rotates the gear 58 to rotate the pivot post 34. Depending upon the direction of rotation of the pivot post, the convolutions of the spring 64 will be tightened or loosened to adjust the bias of the spring.

It is noteworthy that the flat elongated strut sections 36 and 44 are formed from aluminum or similar lightweight, bendable material. Not only does this make the dynamic extension splint 10 light and compact, but it also permits the strut sections to be bent to conform to the outer contour of the limb of a user after the splint is in place to enhance comfort. Also, since the mechanical joint 20 can be disassembled by removing the spring clip 62, the spring 64 can be reversed to reverse the direction in which the spring aids or opposes pivotal movement. This facilitates therapeutic use of the dynamic extension splint 10 to provide either flexion or extension resistance. The spring force can also be reversed by the means described below in connection with FIGS. 23 through 27.

Referring now to FIGS. 6 and 7, a second embodiment of the dynamic splint of the present invention is indicated generally at 78. For purposes of description, structural elements of dynamic splint 78 which are identical in structure and operation to those previously described in connection with dynamic splint 10 will be designated with li  reference numerals. Also, in FIG. 6, only one side dynamic splint 78 is illustrated, but it should be recogni that the first and second strut members and mechanical shown in FIG. 6 are provided on both sides of the susp sleeve 12 as shown in FIG. 2.

Dynamic splint 78 includes a suspension sleeve 12 which differs from that of FIG. 1 in that it is provided with an opening 80 to receive the patella or another portion of a body joint to be treated. The sleeve also includes pull straps on either side connected to one end of the pocket 22. These pull straps, one of which is indicated at 82, are used to pull the sleeve 12 over a limb or a body member.

Dynamic splint 78 differs from dynamic splint 10 mainly in the structure of the mechanical joint, for the splint 78 includes a polycentric mechanical joint 84. This polycentric joint includes two spaced pivot pins 86 and 88 instead of the single pivot post 34 of FIG. 3. Each of these pivot pins extends through one of the bifurcated ends of the strut members 16 and 18. It will be noted that these bifurcated ends do not overlap, as illustrated in FIG. 3, but instead, are spaced apart by the pivot pins 86 and 88. Thus, as illustrated in FIG. 7, the first strut member 16 includes the flat elongate strut section 36, and a bridging section 90 which extends between a lower leg 92 and an upper leg 94. Similarly, the second strut member 18 includes the flat, elongate strut section 44 and a bridging section 96 which extends between a lower leg 98 and an upper leg 100. The bridging sections 90 and 96 space the lower legs 92 and 98 an equal distance from the upper legs 94 and 100, and circular leaf-springs 102 and 104 are mounted about the pivot pins 86 and 88 between the upper and lower legs of the first and second strut members. One end 106 of the spring 102 is hooked about a post 108 that extends between the lower leg 98 and the upper leg 100 of the second strut member 18, while an opposite end 110 of the spring 102 is secured within a slot 112 formed in the pivot pin 86. Similarly, one end 114 of the spring 104 is hooked about a post 116 which extends between the lower leg 92 and upper leg 94 of the first strut member 16, while a second end 118 of the spring is secured within a slot 120 formed in the pivot pin 88.

A housing 122 extends over the bifurcated ends of the first and second strut members 16 and 18 and encloses the polycentric mechanical joint 84. The pivot pins 86 and 88 extend outwardly on either side of the housing and on one side are clipped in place by the removable clips 62. The opposite ends of the pivot pins extend outwardly beyond the housing 122, and bear meshed gear members 124 and 126. These gear members operate to gear the pivot pins 86 and 88 together, and one gear member is mounted on the end of each of the pivot pins to rotate therewith. Secured to the end of each pivot pin and projecting above the respective gear members 124 and 126 is a tool engaging adjustment knob, with two such adjustment knobs being indicated at 128 and 130. These adjustment knobs include a plurality of flat surfaces for engagement with a wrench-type tool that is used to turn the gear members 124 and 126. For example, if the tool engages the adjustment knob 130 and turns the gear 126 in the direction of the arrow in FIG. 6, then both of the pivot pins 86 and 88 are turned by an equal amount due to the mesh between the gears 126 and 128. This adjusts the bias of the springs 102 and 104 an equal amount, and the degree of tension set into the springs may be indicated by indicia 132 on the gear member 124 which cooperates with a stationary indicator 134 formed on the housing 122.

To lock the gear members 124 and 126 in a desired position, a small locking gear 136 is provided on the end of an elongate slide member 138 which slides in a slot 140 formed in the housing 122. The locking gear 136 has teeth which engage the teeth of the gear members 124 and 126 to lock these gears in place. To unlock these gears for purposes of bias adjustment, the slide member 138 is moved to the left in FIG. 6 to disengage the gear 136. The slide member may be manipulated by means of a knob 142 provided on the end thereof opposite to the locking gear 136.

The housing 122 is formed with indentations 144 and 146 to engage the first and second strut members 16 and 18. These indentations provide stops for the strut members in the extended position shown in FIG. 6. However, the two strut members may be moved together to the left in FIG. 6 for a full 180° due to the polycentric construction of the mechanical joint 84. As the strut members pivot, the pivotal movement is transmitted by the posts 108 and 116 to the springs 102 and 104, and these springs oppose pivotal movement between an extended and a closed position in one direction while aiding pivotal movement in the opposite direction. The bias of the two springs may be adjusted equally by rotating one of the gear members 124 or 126 to accomplish rotation of the opposite gear for an equal amount and therefore rotation of the pivot pins 86 and 88.

As in the case of the spring 64, the springs 102 and 104 can be reversed by removing the clips 62 and disassembling the mechanical joint 84. Thus the dynamic extension splint 78 can be configured to provide either flexion or extension resistance.

The dynamic extension splints 10 and 78 may be provided with an adjustable range of motion stop assembly to limit the degree of motion a body member is permitted to make around a body joint. For many types of injuries, it is beneficial to rehabilitate the body joint in stages with the degree of motion permitted by the splints being increased as free motion in a previous stage is achieved. With reference to FIGS. 8–10, the mechanical joint assembly 14 for the dynamic extension splint 10 includes an arcuate line of spaced holes 150 and 152 formed in the legs 38 and 40 respectively. A hole 150 is aligned with a corresponding hole 152 to receive one of the spring biased pins 154 or 156 extending from opposite ends of a stop 158. The stop 158 includes a stop housing 160 that retains the pins 154 and 156 which are biased outwardly from the ends of the stop housing by a spring 162. The stop housing extends across the legs 46 and 48 so that when the pins extend into selected holes 150 and 152, the stop 158 will engage the legs 46 and 48 to limit the relative pivotal movement of the strut members 16 and 18. To remove or adjust the position of the stop 158, the pins 154 and 156 are compressed into the stop housing 160 so that the stop can be disengaged from the holes 150 and 152.

The dynamic extension splint 78 shown in FIGS. 11 and 12 is also provided with a range of motion stop assembly including a plurality of arcuately arranged spaced holes 164 and 166 formed in the upper and lower edges respectively of the housing 122. As shown in FIG. 12, which is a view of a portion of the mechanical joint 84 with the springs 102 and 104 removed for purposes of illustration, two stops 158 are positioned to span the distance between the upper and lower edges of the housing 122, with a stop extending in front of each of the bifurcated ends of the strut members 16 and 18. The spring biased pins 154 and 156 for each stop extend into a hole 164 and 166 respectively in the housing 122. Thus, each stop limits the range of pivotal movement of a strut member 16 or 18 depending upon where the stop is positioned in the line of holes 164 or 166.

FIG. 13 is an exploded view of a preferred embodiment of the mechanical joint 20 which provides a locking means for relieving the action of the bias mechanism during installation and removal of dynamic extension splint 10. In this embodiment, mechanical joint 20 has a hole 170 through housing 56 of mechanical joint 20. A hole 172 of size and shape similar to that of hole 170 is formed in strut member 18, which rotates relative to housing 56 and strut member 16 as explained previously. Holes 170 and 172 are formed at the same distance from the axis of rotation of strut member 18 (i.e. pivot post 34, not shown) so that holes 170 and 172 are aligned, at one point in the rotation of strut member 18 relative to housing 56, along a locking pin insertion axis 174 parallel to the axis of rotation of strut member 18. At the point of alignment of holes 170 and 172, locking pin 176 can be inserted through both holes 170 and 172 to prevent relative motion of strut members 16 and 18. Locking pin 176 comprises knob 178 and elongated pin 180. Of course, a plurality of holes 170 or holes 172 could also be provided to provide several points of alignment at which strut members 16 and 18 could be locked together. Also, holes 170 and 172 and locking pin 176 can be provided on either one or both of the two mechanical joints 20 of a given dynamic extension splint 10, as desired.

In use, locking pin 176, together with holes 170 and 172, can be used to remove the bias force provided by mechanical joint 20 during attachment and removal of dynamic extension splint 10 from the affected body part. The elimination of the bias force during attachment and removal simplifies the attachment and removal process, particularly when larger bias forces are being applied. Specifically, any bias force components tending to act against the forces needed to disengage components of dynamic extension splint 10 from the affected body part will be neutralized. This neutralization of bias forces also prevents any springing back of strut members 16 or 18 when one of strut members 16 or 18 is released from the affected body part and the other is still attached. Such springing action as a result of bias forces during removal of the device could aggravate the injuries being treated with dynamic extension splint 10, or cause further injuries. Of course, bias force could also be reduced by adjusting the tension on mechanical joints 20. However, the use of locking pin 176 permits complete elimination of the bias force without disturbing the desired bias force setting.

Industrial Applicability

The dynamic splint of the present invention is used for the treatment of joint contractures occurring secondary to trauma, casting, or other immobilization. It is also used to restore strength and flexibility to a body joint, by creating resistance requiring the wearer to flex the joint, thereby building strength and fluidity. The bias adjustment feature incorporated within the dynamic extension splint permits the spring bias of the splint to be varied throughout a recovery process as treatment of the joint progresses.

The dynamic splints disclosed permit maintenance of a defined tolerable force level with maximum linearity over a wide range of motion of a body joint. The dynamic splints are particularly useful for prophylactic maintenance of range-of-motion and mobility, particular in post-operative cases.

We claim:

1. A bias adjustment assembly for an adjustable splint device having a first splint strut member, a second splint strut member, a joint assembly for mounting said first and second strut members for relative pivotal movement and a bias unit having a first end and a second end, the bias unit operating to oppose relative pivotal movement of said strut members in a first direction, the bias adjustment assembly comprising:

a mounting unit mounted at said joint assembly, a rotatable adjustment unit including an elongate adjustment shaft mounted on said mounting unit, and a gear member having gear teeth mounted on said adjustment shaft for rotation, and an elongate rotatable actuator mounted for rotation on said mounting unit, said rotatable actuator having threads which mesh with said gear teeth of said gear member to rotate said gear member to one of a plurality of rotational positions and to hold said gear member in a rotational position when said rotational actuator ceases to rotate, the first end of said bias unit being attached to said rotatable adjustment unit and said bias unit being adapted to wrap around said adjustment shaft as said rotatable adjustment unit is rotated to increase the bias of said bias unit.

2. The bias adjustment assembly of claim 1 wherein said gear member includes an indica bearing face having a plurality of spaced indicia formed thereon, said mounting unit including at least one viewing opening to expose at least one of said spaced indicia, said spaced indicia being arranged to pass sequentially under said viewing opening as said gear member is rotated.

3. The bias adjustment assembly of claim 1 wherein said rotatable actuator is formed by an adjustment screw mounted to tangentially engage said gear member.

4. The bias adjustment assembly of claim 3 wherein said mounting unit includes an enclosure mounted on one of said strut members, said elongate adjustment shaft, gear member and adjustment screw being mounted within said enclosure.

5. The bias adjustment assembly of claim 4 wherein said gear member includes an indicia bearing face having a plurality of spaced indicia formed thereon, said enclosure including at least one viewing opening to expose at least one of said spaced indicia, said spaced indicia being arranged on said indicia bearing face to pass sequentially under said viewing opening as said gear member is rotated.

6. The bias adjustment assembly of claim 5 wherein said bias unit includes a spring.

7. The bias adjustment assembly of claim 4 wherein said elongate adjustment shaft is mounted for rotation with said gear member, the first end of said bias unit being attached to said elongate adjustment shaft.

8. An adjustable splint device for applying force across a body joint comprising:

a first strut member;

a second strut member;

a joint assembly connecting said first and second strut members for relative pivotal movement about a pivot axis;

a bias unit connected at said joint assembly to oppose relative pivotal movement of said first and second strut members in at least one direction, said bias unit having a first end connected to said joint assembly to move circumferentially around said pivot axis during relative pivotal movement of said first and second strut members; and a bias adjustment assembly connected to said bias unit to adjust the bias thereof; said bias adjustment assembly including a mounting unit, an elongate rotatable adjustment shaft mounted for rotation on said mounting unit, said rotatable adjustment shaft engaging said bias unit to vary the bias thereof upon rotation of said rotatable adjustment shaft, and an indicator unit having an indicia bearing face with a plurality of spaced indicia formed thereon, said indicia being arcuately arranged in sequence on said indicia bearing face, said indicator unit being secured to said rotatable adjustment shaft for rotation therewith.

9. The adjustable splint device of claim 8 which includes a gear mechanism mounted for rotation with said adjustment shaft and a gear engagement unit mounted on said mounting means to engage said gear.

10. The adjustable splint device of claim 9 wherein said joint assembly includes a locking mechanism spaced from said pivot axis and operable for preventing relative pivotal movement of said first and second strut members.

11. The adjustable splint device of claim 10 wherein said locking mechanism operates to lock said first and second strut members at a plurality of angular positions along an arc of pivotal rotation between said first and second strut members.

12. The adjustable splint device of claim 11 wherein said bias unit includes a spring.

13. An adjustable splint device for applying force across a body joint comprising:
   a first strut member;
   a second strut member;
   a joint assembly connecting said first and second strut members for relative pivotal movement about a pivot axis;
   a bias unit connected at said joint assembly to oppose relative pivotal movement of said first and second strut members in at least one direction, said bias unit having a first end connected to said joint assembly to move circumferentially around said pivot axis during relative pivotal movement of said first and second strut members; said joint assembly including a connector unit connected to the first end of said bias unit and mounted for rotation about said pivot axis, and a gear secured to said connector unit for rotation therewith; and
   a bias adjustment assembly to adjust the bias of said bias unit, said bias adjustment assembly being mounted on said first strut member and including a rotatable actuator mounted for rotation and having threads which mesh with said gear whereby rotation of said actuator rotates said gear and connector unit about said pivot axis,
   said bias unit having a second end which is connected to said second strut member.

14. The adjustable splint device of claim 13 wherein said gear includes an indicia bearing face with a plurality of spaced indicia formed thereon, said indicia being arcuately arranged in sequence radially outwardly from said pivot axis on said indicia bearing face.

15. The adjustable splint device of claim 14 wherein said gear is circular in shape and includes peripheral gear teeth, said rotatable actuator being formed by an adjustment screw mounted to tangentially engage said gear.

16. The adjustable splint device of claim 15 wherein said joint assembly includes a locking mechanism spaced from said pivot axis and operable for preventing relative pivotal movement between said first and second strut members, said locking mechanism including at least one main locking aperture on said first strut member and a plurality of arcuately arranged, spaced locking apertures on said second strut member positioned to pass sequentially beneath said main locking aperture when relative rotation of said first and second strut members occurs about said pivot axis.

17. An adjustable splint device for applying force across a body joint comprising a first strut member having a longitudinal axis extending between opposed ends thereof, a second strut member having a longitudinal axis extending between opposed ends thereof, a joint assembly for mounting said first and second strut members for relative pivotal movement whereby at least one of said strut members pivots about a pivot axis which is transverse to the longitudinal axes of said first and second strut members, said joint assembly including a joint enclosure mounted at said pivot axis, a bias assembly mounted in said joint enclosure including a bias spring, connection means connecting said bias spring to one of said first and second strut members to provide a bias to oppose pivotal movement of said first and second strut members in a first direction and to aid said pivotal movement in a second direction opposite to said first direction, said bias spring having a first end and a second end, said second end being connected by means of said connection means to one of said first and second strut members, and a bias adjustment unit mounted within said joint enclosure, and an indicator connected to said bias adjustment unit to indicate bias provided by said bias spring,
   said bias adjustment unit having a rotatable adjustment assembly including an elongate adjustment shaft mounted on said joint enclosure, a gear member having gear teeth, said gear member being mounted on said adjustment shaft for rotation and an elongate, rotatable actuator mounted for rotation on said joint enclosure, said rotatable actuator mounted for rotation on said joint enclosure, said rotatable actuator having threads which mesh with the gear teeth of said gear member to rotate said gear member to one of a plurality of rotational positions and to hold said gear member in a rotational position when said rotatable actuator is not rotating, the first end of said bias spring being attached to said rotatable adjustment assembly whereby the bias of said bias spring is varied by the rotation of said rotatable adjustment assembly and said indicator being connected for rotation with said rotatable adjustment assembly to provide a bias indication for said bias spring at different positions of said rotatable adjustment assembly.

18. The device of claim 17 which includes locking means for selectively preventing relative pivotal movement of said first and second strut members.

19. The device of claim 18 wherein said locking means is operative to lock said first and second strut members against relative pivotal movement at a plurality of spaced angular positions along an arc of pivotal rotation between said first and second strut members.

20. The device of claim 17 wherein said indicator is mounted within said joint enclosure and bears a plurality of spaced indicia, said joint enclosure including at least one viewing opening to expose at least one of said spaced indicia, said spaced indicia being arranged to pass sequentially under said viewing opening as said indicator is rotated.

21. The adjustable splint device of claim 17 wherein said rotatable actuator is mounted to tangentially engage said gear member, said indicator being mounted on said gear member.

22. The adjustable splint device of claim 21 wherein said bias spring is a spiral spring formed to provide a plurality of overlapping circular coils between the first and second ends thereof, said coils encircling said elongate adjustment shaft, said joint enclosure being mounted on a first strut member and the second end of said bias spring being connected by said connection means to said second strut member.

23. The adjustable splint device of claim 22 wherein said elongate adjustment shaft is mounted for rotation with said gear member, the first end of said bias spring being attached to said elongate adjustment shaft.

24. The device of claim 22 wherein said indicator is mounted within said joint enclosure and bears a plurality spaced indicia, said joint enclosure including at least one viewing opening to expose at least one of said spaced indicia, said spaced indicia being arranged to pass sequentially under said viewing opening as said indicator is rotated.

* * * * *